May 10, 1960 T. K. SAND Plant Pat. 1,941
PEACH TREE
Filed Oct. 27, 1958
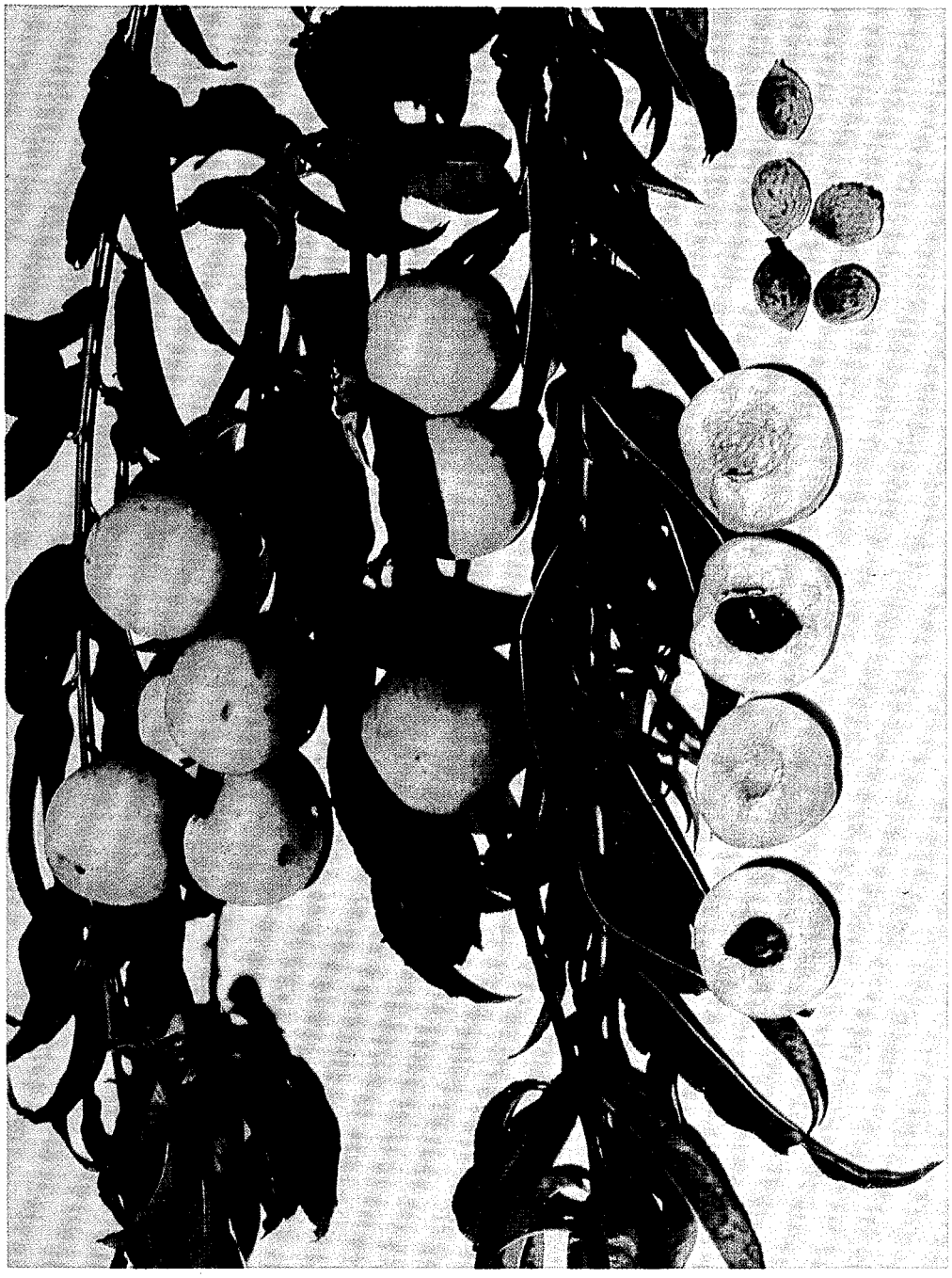
THEODORE K. SAND
INVENTOR
HUEBNER & WORREL
ATTORNEYS
BY Richard M. Worrel United States Patent Office Plant Pat. 1,941
Patented May 10, 1960

1,941

PEACH TREE

Theodore K. Sand, Delano, Calif.

Application October 27, 1958, Serial No. 769,961

1 Claim. (Cl. 47—62)

The present invention relates to a new and distinct variety of peach tree of the light-fleshed, greenish-yellow skinned, freestone fruit type and more particularly to such a peach tree characterized by the production of seeds having special advantages as seedling rootstock.

It is well-known that most seedling rootstocks for peach trees are subject to serious damage by nematodes. The problem of nematode resistance has been one which has long confronted nurserymen and farmers. Further, present commercial seeds intended for rootstock germinate unevenly and produce seedlings of widely varied characteristics which grow unevenly and make nursery care difficult. For example, one type of commercially popular seeds for peach seedlings is obtained from a well-known potential peach tree. These seeds have such widely varied characteristics that when germinated and the resultant seedlings grow to maturity they produce peaches and even nectarines of widely varied color, shape, size and other characteristics.

An object of the present invention was, therefore, to produce a peach tree characterized by the production of seed having improved and substantially uniform germinating characteristics.

Another object was to provide a peach tree producing seeds from which seedlings resistant to nematodes could be obtained.

Another object was to provide a peach tree whose seeds are substantially uniform and which produces seedlings of improved uniformity and consistency to type.

Another object was to provide a peach tree which is a regular and heavier bearer of small freestone fruits which are easy to gather and from which the seeds are easily extracted.

Another object was to provide a peach tree capable of producing progeny which have vigorous root systems and are vigorous in growing habits.

Another object was to provide a peach tree which is remarkably uniformly resistant to nematodes, crown gall disease, damage incident to excessive irrigation, and resistant and tolerant of other diseases, adverse environmental conditions, and cultural abuses.

The attainment of the foregoing and other objects and advantages will become more fully apparent upon reference to the drawing and following description.

The instant variety of peach tree resulted from a planned and deliberately followed procedure directed to the attainment of improved peach tree seedlings. A number of open pollinated F–1 seed of a variety known as the S–37 from peach trees of Plant Patent 904, were obtained and germinated. Two hundred and three of the resultant seedlings were planted in an orchard near McFarland, California. Without budding or grafting, this orchard was brought into bearing and each tree subjected to careful scrutiny and evaluation over a period of four years. For an additional two-year period, the apparently superior trees in the orchard were observed and subjected to numerous tests under both nematode nursery and orchard conditions. It was ultimately discovered that one of the seedling trees was markedly superior in nematode and disease resistance and possessed desired vigorous growth. Seeds from this single selected tree were then grown in a nursery row. When ready for budding, the scions were taken from the original parent tree for the purpose of creating a mother orchard of identical origin and entirely free of disease. This asexual reproduction of the peach tree occurred at Rancho Fortuna, near the city of McFarland, county of Kern, State of California. The resultant budded trees were carefully examined and found consistently to possess the characteristics of the selected tree.

The drawing shows specimens of leaves growing on first and second year branches, characteristic fruit, a peach cut transversely of the suture plane and open for inspection of both resultant halves, a peach cut on suture plane and likewise opened for inspection, and characteristic stones, all of the new variety.

The most striking characteristics of the new peach tree is its transmission to its seed progeny substantially uniform characteristics of growth, desirable budding traits, uniformity of bearing, resistance to nematodes generally and virtually complete resistance to certain types of nematodes, resistance to crown gall, and tolerance of adverse environmental conditions.

These characteristics are conveniently exemplified by reference to three tests which have been conducted. Seeds of the S–37, Lovell, and the subject variety were planted in nursery rows near Wasco, California under standard nursery procedures. The seeds of the subject variety and the S–37 were planted in uniformly spaced relation while the seeds of the Lovell were planted more thickly and then thinned to the same spaced relation. This is in accordance with normal nursery practice because of the low rate of germination of the Lovell seeds. The seeds were planted at the same depth, in the same type of soil, and grown under as precisely the same growing conditions as possible. By May 16, the seedlings had reached nearly budding size. Care was taken to select as nearly typical sections of the rows of the three varieties as possible, and photographs were taken thereof. Each photograph covered approximately seven feet of its respective row. By measurement, it was found that the Lovell seedlings varied approximately 50% in height, the S–37 seedlings from 25% to 30% in height, and the subject variety less than 10% in height. These variations in vigor of growth are typical of the varieties so compared.

As a second test, in the spring of 1958, 230,400 seeds of the subject variety were planted at the same time and under the same conditions as approximately 181,440 Lovell seeds in an adjacent field. At the June budding season, all of the seedlings of both varieties were budded. The same budding crews were used on both varieties of root stock and the bud wood came from the same source. 141,128 of the subject variety seedlings budded successfully. This is 61.2% of the seed sown. 67,395 of the Lovell seedlings were successfully budded, a percentage of 37.1% of the seed sown. It is noted that the subject variety budded successfully 24.1% more frequently than the Lovell.

Of the 141,128 seedlings of the subject variety which budded successfully, 123,231 reached maturity as nursery stock and dug-out as salable trees, a percentage of 87.3%. Of the 67,395 Lovell seedlings successfully budded, 43,381 reached maturity and dug-out as salable trees, a percentage of 64.3%. The 23% better maturation of the subject variety is believed due to its vigorous growing habits and resistance to disease and virus.

The resultant trees borne by the subject variety and the Lovell variety root stocks were carefully graded for sale. It is well-known in nursery and farm circles that June buds of from 5/16" to 3/8" in caliber are more easily sold and are known as "prime." The demand for those having a caliber of from ¼" to 5/16" is less and such trees are more difficult to sell. Of the 123,231 trees on the subject variety root stock, 108,044 dug-out as 5/16" to ⅜" caliber or better, a percentage of 87.6%. Of the 43,381 trees on the Lovell root stock 27,289 dug-out at 5/16" to ⅜" caliber or better, a percentage of 64.1%. The substantial greater percentage of prime trees grown on the subject variety root stock as compared with the Lovell root stock is a significant advantage in nursery operations.

A third test was conducted to evaluate the resistivity of the subject variety to nematodes. The test was conducted by Dr. Carl J. Hansen, professor of pomology, and Dr. Benjamin Lounsbury, professor of nematology, at the University of California at Davis, California. Two tanks of sterilized soil were prepared. The soil of the first tank was impregnated with *Meloidogyne javanica* nematode culture and that of the second tank with *Meloidogyne incognita* var. *acrita* nematode culture. Seeds of the subject variety, Lovell and S-37 were sown in each of the tanks in individual rows, germinated, and grown for the same period under precisely identical cultural conditions. The seedlings were dug at the same time and their roots carefully inspected and graded with respect to nematode infestation in accordance with the following scale.

0—No infection found
1—Slight galling
2—Moderate galling
3—Damaging galling
4—Severe galling
5—Completely infected The following results were noted:

SOIL IMPREGNATED WITH *MELOIDOGYNE JAVANICA*

| Row | Variety | No. Trees | Aver. Height (cm.) | Aver. Grade |
|---|---|---|---|---|
| 8 | Subject Variety | 18 | 84.9 | 3.1 |
| 17 | Lovell | 20 | 73.3 | 3.6 |
| 18 | S-37 | 12 | 82.1 | 3.4 |

SOIL IMPREGNATED WITH *MELOIDOGYNE INCOGNITA* VAR. *ACRITA*

| | | | | |
|---|---|---|---|---|
| 5 | S-37 | 12 | 92.8 | (*) |
| 8 | Subject Variety | 19 | 99.2 | 0 |
| 9 | Lovell | 17 | 40.9 | 4.8 |
| 17 | Lovell | 3 | 33.7 | 5.0 |
| 18 | S-37 | 10 | 95.4 | 0 |

*Not averaged, several galls found.

These results show that the subject variety has a resistance to *Meloidogyne javanica* nematodes substantially better than Lovell root stock and materially better than S-37 root stock. Its resistance to *Meloidogyne incognita* var. *acrita* nematodes, the well-known root knot nematodes, is vastly superior to the Lovell and as good or better than the S-37. None of the specimens of the subject variety showed any infestation by this latter nematode while a few of the S-37 did. Further, the results of this test shown average heights of the subject variety at the time of the tests substantially greater than the average heights of the Lovell and S-37 seedlings.

Referring more specifically to the pomological details of the new and distinct variety of peach tree with all major color identifications being by reference to Maerz and Paul Dictionary of Color, the following characteristics occurring under the ecological conditions prevailing at the designated location of the asexual reproduction are noted:

Parentage: One parent was the seedling peach tree known as S-37 of Plant Patent No. 904 and the other parent is unknown.

Tree:
*Size.*—Large.
*Figure.*—Form and density controlled by pruning but tends to be rounded and somewhat globular displaying unusually resilient limbs markedly drooping when weighted by crop but returning to upright positions when relieved of weight.
*Productivity.*—Highly productive and regular bearer under standard orchard conditions.
*Trunk.*—Usually stocky and characteristic gray color of peach trees and other medium size.

Branches:
*Size.*—Long and slender; upright; resiliently drooping under load.
*Color.*—Green (17-I-7 to 17-K-5) when young and throughout most of first year, later overlaid with leather brown color (14-A-10) becoming unidentifiable gray when old.
*Lenticels.*—Number—more numerous than on most peach trees. Size—medium.

Leaves:
*Size.*—Markedly varying but generally medium when mature.
*Length.*—Average 5½" to 6½".
*Width.*—Average ⅞" to 1⅜".
*Shape.*—Lanceolate with acuminate tip.
*Color.*—Upper side somewhat more yellowish green than usual peach trees (21-L-8), lower side lighter yellowish green (21-L-4).
*Marginal form.*—Creanate.
*Glandular characteristics.*—Minute reniform; confined principally to juncture of leave and petiole; greenish yellow in color (21-L-8); usually occurring in pairs but sometimes three or four in number.
*Petiole.*—Length—medium to short, ½" to ¼". Thickness—medium. Stipules—average ⅜" light green generally prevalent.

Blossom buds: Medium large, long, free pubescent.

Blossoms:
*Date of bloom.*—Late, about February 27.
*Size.*—Large, comparable to Fay Elberta, single.
*Color.*—White.

Fruit:
*Maturity.*—Picking ripe average August 31.
*Size.*—Uniformity—unusually uniform. Longitudinal diameter—average 2 1/16". Diameter transversely in suture plane—average 1⅞". Diameter transversely in plant at right angles to suture plane—average 2 1/16".
*Form.*—Uniformity — consistent. Symmetrical—usually so. Suture—distinct, shallow, extending from stem to pistil point. Ventril surface—Slightly lapped with laps substantially equal. Stem cavity—shallow. Base—globular. Apex—globular with minute pistil point. Stem—short, stocky, relatively firmly affixed to pit.

Skin:
*Thickness.*—Thick, tough.
*Tendency to crack.*—None observed.
*Color.*—Greenish-yellow (17-E-3) to white (17-D-1) tending toward yellow (17-G-1) when dead ripe.
*Pubesence.*—Considerable.

Flesh:
*Color.*—White (17-C-1) to straw (10-F-2) to greenish-white (18-G-3) when fully ripe.
*Surface of pit cavity.*—Rounded, average depth 1"; average breadth approximately ¾"; average thickness ⅝".
*Color of pit well.*—Greenish white (18-G-3) to light straw (10-F-2).
*Amygdalin.*—Present.
*Juice.*—Abundant.
*Flavor.*—Poor.

*Aroma.*—Lacking.
*Texture.*—Coarse.
*Fibers.*—Moderate.
*Ripening.*—Uniform.
*Eating quality.*—Poor.

Stone:
*Free or cling.*—Markedly free.
*Fibers.*—Few adherent.
*Size.*—Average length 1"; average breadth ¾"; average thickness ⅝".
*Form.*—Obovate.
*Hilum.*—Oval.
*Apex.*—Minutely acuminate.
*Sides.*—Symmetrical.
*Surface.*—Regularly grooved.
*Color.*—Light tan or brown (4–A–12).
*Splitting tendency.*—Negligible.
*Taste of kernel.*—Mildly bitter.

Use: Production of seeds for rootstock seedlings.
Resistance to disease: Marked resistance to nematode infections, crown gall and difficulties normally incident to excessive irrigation.

It is to be understood that the tree herein described, its fruit, and its progeny may vary in certain respects due to variations in climate, soil or other environmental conditions but that such variations should not obscure the identity of the new variety as set forth in the claim which should be accorded its full scope so as to embrace all of the defined peach trees even when subjected to such ecological variations.

Having described my new peach tree, I claim:

A new and distinct variety of peach tree of the white-fleshed, greenish-yellow skinned, freestone fruit type, substantially as herein shown and described, characterized particularly by the production of seeds having substantially uniform germination characteristics productive of more uniform seedlings having greater resistance to nematodes than other known drupe rootstocks including its parent known as the S–37 rootstock of United States Plant Patent No. 904.

No references cited.

Dedication

Plant Patent 1,941.—*Theodore K. Sand*, Delano, Calif. PEACH TREE. Plant patent dated May 10, 1960. Dedication filed Sept. 10, 1970, by the assignee, *Armstrong Nurseries, Inc.*

Hereby dedicates the entire patent to the Public of the United States.

[*Official Gazette October 27, 1970.*]